United States Patent

Segaud et al.

[11] Patent Number: 6,121,193
[45] Date of Patent: Sep. 19, 2000

[54] COMPOSITION FOR THE TREATMENT OF RICE SEEDS

[76] Inventors: Christian Segaud, 3 impasse la Fontaie, 69710 Genas; Francois Farre, Lieu Dit "les a Chopines ", Lucenay, both of France

[21] Appl. No.: 08/938,804

[22] Filed: Sep. 26, 1997

[30] Foreign Application Priority Data

Sep. 26, 1996 [FR] France .................. 96 11970

[51] Int. Cl.$^7$ .......... A01N 25/26; A01N 63/00; A01N 43/36; A01N 43/56
[52] U.S. Cl. .......... 504/100; 504/118; 504/138; 504/280; 504/282
[58] Field of Search ............... 504/100, 118, 504/138, 280, 282

[56] References Cited

U.S. PATENT DOCUMENTS

| | | | |
|---|---|---|---|
| 4,272,417 | 6/1981 | Barke et al. | 260/22 |
| 4,658,539 | 4/1987 | Sluis | 47/57.6 |
| 4,808,215 | 2/1989 | Gill et al. | 71/105 |
| 5,441,735 | 8/1995 | Takahara et al. | 424/93.2 |
| 5,567,429 | 10/1996 | Senbo | 424/405 |

FOREIGN PATENT DOCUMENTS

| | | |
|---|---|---|
| 54608/96 | 12/1996 | Australia . |
| 0 295 117 | 6/1988 | European Pat. Off. . |
| 2696904 | 4/1994 | France . |
| 2696906 | 4/1994 | France . |
| 07149606 A2 | 6/1995 | Japan . |
| 969962 | 9/1964 | United Kingdom . |
| WO 87/03781 | 7/1987 | United Kingdom . |
| WO 93/06089 | 4/1993 | United Kingdom . |
| WO 94/21606 | 9/1994 | United Kingdom . |

OTHER PUBLICATIONS

Copy of French Search Report.

*Primary Examiner*—Jose' G. Dees
*Assistant Examiner*—Alton Pryor
*Attorney, Agent, or Firm*—Morgan & Finnegan, L.L.P.

[57] ABSTRACT

Agrochemical compositions, characterized in that they comprise from 0.5 to 50%, preferably from 1 to 20%, by weight of at least one agrochemical active material of formula (I):

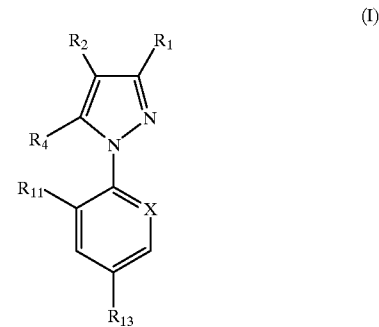

in which the substituents are as defined in the description, and an effective amount of a high-molar-mass hyper-branched polymer, for use in the treatment of rice seeds.

22 Claims, No Drawings

COMPOSITION FOR THE TREATMENT OF RICE SEEDS

The subject of the present invention is a novel agrochemical composition useful in the treatment of rice seeds and a method for the protection of rice crops employing it.

The closest prior art to that of the present invention is illustrated by Patent GB-969,962, which describes fungicidal compositions in the form of a powder containing Zineb (zinc ethylenebisdithio-carbamate) mixed with very small amounts of a water-dispersible, cationic, nitrogen-containing polymer. The aim of these compositions is to improve the storage properties and to facilitate the application of the active material.

U.S. Pat. No. 4,808,215 describes a method intended to improve the floatability of a herbicidal suspension by addition of a water-soluble polymer.

Finally, U.S. Pat. No. 5,441,735 claims a pesticidal agent which acts by mutagenesis, it being possible for high-molecular-weight and water-soluble synthetic chemical compounds to be added to this pesticidal agent in order to enhance its wettability.

It is commonplace for rice growers to apply an agrochemical active material to seeds in order in articular to protect the latter from pests and/or to increase the yields.

This application is carried out, before sowing, either directly on the seeds or after having pregerminated the latter, this pregermination being intended to promote even and homogeneous growth of the seedlings, which is particularly easy in rice cultivation. This pregermination phase comprises steeping rice grains or seeds in water for a time generally of between 24 and 48 hours and at a temperature varying between 25° C. and 35° C.

According to an often widespread practice, this phase of pregermination of rice seeds is carried out, or continued, by growers, after the agrochemical treatment, by allowing the seeds to stand for 24 to 48 hours before sowing. It is necessary, during this stage, to sprinkle the seeds with water regularly, in order to prevent the warming of the seeds resulting from the germination and which is capable of hindering the subsequent growth of the seedlings.

This phase of sprinkling with water exhibits, however, the disadvantage of leaching out and thus very greatly reducing the amount of agrochemical active material attached to the seed, which goes against the desired aim relating to protecting the crop against pests.

Moreover, an even minimum amount of agrochemical active material present in the water can sometimes pose problems of environmental pollution.

One aim of the present invention is to provide an agrochemical composition which overcomes the disadvantages stated above.

Another aim of the present invention is to provide an agrochemical composition which ensures the adhesion of the agrochemical active material or materials to the rice seeds, even after the treated seeds have been sprinkled with water.

Another aim of the present invention is to provide an agrochemical composition which reduces the environmental risks related to the sprinkling with water of seeds treated with an agrochemical active material before sowing and/or after sowing.

Another aim of the present invention is to provide an agrochemical composition which reduces the environmental risks related to the sowing of the treated seeds in flooded rice paddies.

It has now been found that these aims could be achieved in all or in part by virtue of the agrochemical compositions according to the invention.

A first subject of the invention is therefore agrochemical compositions, characterized in that they comprise:

A) from 0.5 to 50%, preferably from 1 to 20%, by weight of at least one agrochemical active material of the family of the 1-arylpyrazoles of formula (I):

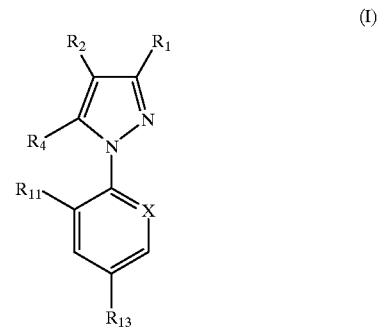

in which:

$R_1$ represents a halogen atom or a CN or methyl group;

$R_2$ represents $S(O)_n R_3$ or 4,5-dicyanoimidazol-2-yl or haloalkyl;

$R_3$ represents alkyl or haloalkyl;

$R_4$ represents a hydrogen or halogen atom or an $NR_5R_6$, $S(O)_m R_7$, $C(O)R_7$ or $C(O)O-R_7$, alkyl, haloalkyl or $OR_8$ radical or an $-N=C(R_9)$ $(R_{10})$ radical;

$R_5$ and $R_6$ independently represent a hydrogen atom or an alkyl, haloalkyl, C(O)alkyl, $C(O)OR_7$ or $S(O)_r CF_3$ radical or $R_5$ and $R_6$ can together form a divalent alkylene radical which can be interrupted by one or two divalent heteroatoms, such as oxygen, nitrogen or sulphur;

$R_7$ represents an alkyl or haloalkyl radical;

$R_8$ represents an alkyl or haloalkyl radical or a hydrogen atom;

$R_9$ represents an alkyl radical or a hydrogen atom;

$R_{10}$ represents a phenyl or heteroaryl group optionally substituted by one or more halogen atoms or groups such as OH, —O-alkyl, —S-alkyl, cyano or alkyl;

$R_{11}$ and $R_{12}$ represent, independently of one another, a hydrogen or halogen atom or CN or $NO_2$;

$R_{13}$ represents a halogen atom or a haloalkyl, haloalkoxy, $S(O)_q CF_3$ or $SF_5$ group;

m, n, q and r represent, independently of one another, an integer equal to 0, 1 or 2;

X represents a trivalent nitrogen atom or a $C-R_{12}$ radical, the other three valencies of the carbon atom forming part of the aromatic ring;

with the proviso that, when $R_1$ is methyl, then either $R_3$ is haloalkyl, $R_4$ is $NH_2$, $R_{11}$ is Cl, $R_{13}$ is $CF_3$ and X is N or else $R_2$ is 4,5-dicyanoimidazol-2-yl, $R_4$ is Cl, $R_{11}$ is Cl, $R_{13}$ is $CF_3$ and X is C—Cl, and B) an effective amount of a high-molar-mass hyperbranched polymer.

In the formula (I) defined above, the alkyl and alkoxy radicals and moieties generally comprise from 1 to 6 carbon atoms and the ring formed by the divalent alkylene radical representing $R_5$ and $R_6$ and by the nitrogen atom to which $R_5$ and $R_6$ are attached is generally a 5-, 6- or 7-membered ring.

The compounds of formula (I) are particularly advantageous because of their insecticidal properties, in combating various insects and nematodes which are parasites of rice, and fungicidal properties and as growth regulators for rice.

A preferred class of compounds of formula (I) is composed of the compounds in which $R_1$ represents CN and/or $R_3$ represents haloalkyl and/or $R_4$ represents $NH_2$ and/or $R_{11}$ and $R_{12}$ represent, independently of one another, a halogen atom and/or $R_{13}$ represents haloalkyl.

A compound of formula (I) which is very particularly preferred in the invention is 1-[2,6-$Cl_2$-4-$CF_3$phenyl]-3-CN-4-[SO—$CF_3$]-5-$NH_2$pyrazole, subsequently known as "Compound A".

Compounds of formula (I) can be prepared according to one or other of the methods described in Patent Applications WO 87/3781, 93/6089 and 94/21606 or European Patent Application 295,117 or any other method coming within the competence of a person skilled in the art of chemical synthesis.

The term hyperbranched polymer means that the polymer possesses a high degree of branching. Representatives of this type of hyperbranched polymer are, for example, polyethyleneamines, polyamidoamides, polyethyleneimines, polyethers, copolymers deriving from these polymers, and the like.

Moreover, the term hyperbranched polymer must be understood as, in addition, encompassing hyperbranched polymers which have been subjected to chemical conversions, such as, for example, crosslinking, graftings, for example of hydroxyl, anionic or lipophilic groups, or any other chemical modification appropriate to the needs of the invention and known to an expert in the synthesis of polymers.

Of course, this list is not limiting, however, and all the types of hyperbranched polymers known to a person skilled in the art come within the scope of the present invention.

High-molar-mass polymer is understood to mean polymers with a mean molar mass generally of between 200 and 5,000,000 grams, preferably between 300 and 3,000,000 grams and more preferably still between 800 and 2,000,000 grams.

The hyperbranched polymer employed in the agrochemical compositions according to the invention will preferably be in the form of an aqueous suspension.

All these hyperbranched polymers are known to a person skilled in the art and are commercially available.

A type of hyperbranched polymer which is appropriate for the agrochemical compositions according to the invention comprises polyethyleneimines optionally modified by chemical conversions, such as, for example, crosslinking, graftings, for example of hydroxyl, anionic or lipophilic groups, or any other chemical modification appropriate to the needs of the invention and known to an expert in the synthesis of polyethyleneimines.

The polyethyleneimine employed in the agrochemical compositions according to the invention will preferably be in the form of an aqueous suspension.

A particularly preferred class of polyethyleneimines comprises the polymers obtained by polymerization of aziridine or of its derivatives.

The particularly appropriate polyethyleneimines have a molar mass of from 200 to 5,000,000 and more particularly from 300 to 3,000,000.

More preferably still, the polyethyleneimines used in the agrochemical compositions of the present invention exhibit a molar mass of from 800 to 2,000,000.

Polyethyleneimines which are very particularly suited to the agrochemical compositions according to the present invention are those with the trademarks Lupasol® or Polymin® sold by the company BASF.

Surprisingly, the combination of a hyperbranched polymer with one or more agrochemical active materials defined by the formula (I) makes it possible, unlike the adhesion agents generally used in seed treatment, to improve the adhesion of the said active materials to the seeds after sprinkling with water.

An effective amount of hyperbranched polymer ensuring adhesion of the agrochemical active material to rice seeds after sprinkling with water is understood to mean an amount greater than 50%, preferably greater than 65%, more preferably still greater than 75% by weight of the agrochemical combination of the invention.

This adhesion after sprinkling with water is defined by the following test:

Test of adhesion after sprinkling with water:

1 kg of rice seeds are immersed in water at 32° C. for 48 hours. The pregerminated seeds thus obtained are drained for 3 hours. 100 g of these seeds are then removed.

Moreover, an amount of a composition according to the invention is removed and is diluted, if appropriate, with water, so as to obtain a treatment liquid containing 25 mg of agrochemical active material as defined by the formula (I).

The said amount of treatment liquid is applied, with mixing, to the 100 g of drained seeds.

Sprinkling is simulated by the following procedure: after draining for 2 hours, 40 g of seeds, thus treated, are introduced into a measuring cylinder containing 250 ml of water. This measuring cylinder is stoppered and then subjected to 5 inversions about a horizontal axis. Inversion is understood to mean a rotational movement of 180° downwards, followed by a rotational movement of 180° in the opposite direction upwards. The seeds are then collected, then dried for 15 hours at 30° C., and the amount of agrochemical active material attached to the seeds is determined by HPLC-type chromatography.

The degree of adhesion after sprinkling is equal to the weight of agrochemical active material thus found divided by the weight of active material applied. This degree of adhesion after sprinkling is expressed as percentage by weight.

In practice, an amount of hyperbranched polymer corresponding to a weight of polymer/weight of agrochemical active material ratio of from 0.01 to 5, preferably from 0.01 to 0.5, gives good adhesion results after sprinkling with water.

In addition to the active material of formula (I) defined above and the hyperbranched polymer, the compositions according to the invention can contain one or more other agrochemical active materials used in the cultivation of rice, preferably water-insoluble, solid active materials.

These active materials can be plant protection agents, pesticides, growth regulators or plant nutritional agents. The pesticides are more particularly herbicides, insecticides, fungicides, nematocides and acaricides.

According to a preferred alternative form of the compositions according to the invention, the additional agrochemical active materials are chosen from insecticides or fungicides which can be applied in the treatment of rice seeds.

In addition to the agrochemical active material or materials described above and the hyperbranched polymer, the agrochemical compositions according to the invention can also contain one or more agriculturally acceptable solid or liquid vehicles and/or one or more agriculturally acceptable surface-active agents.

The term "vehicle", in the present account, denotes a natural or synthetic, organic or inorganic material with which the agrochemical active material and the polymer are combined in order to facilitate their application to the rice seeds. This vehicle is therefore generally inert and it must be agriculturally acceptable, in particular on the treated seeds. The vehicle can be a water-soluble or water-insoluble solid (clays, natural or synthetic silicates, silica, resins, polymers, waxes, solid fertilizers, and the like) or a liquid (in particular water).

The surface-active agent can be a dispersing or wetting agent and is preferably of non-ionic type chosen from:

- ethoxylated or ethoxy-propoxylated fatty alcohols,
- copolymers of ethylene oxide and of propylene oxide,
- ethoxylated or ethoxy-propoxylated triglycerides,
- ethoxylated or ethoxy-propoxylated fatty acids,
- ethoxylated or ethoxy-propoxylated esters of sorbitan,
- ethoxylated or ethoxy-propoxylated fatty amines,
- ethoxylated or ethoxy-propoxylated di(1-phenylethyl) phenols,
- ethoxylated or ethoxy-propoxylated tri(1-phenylethyl) phenols, and
- ethoxylated or ethoxy-propoxylated alkylphenols.

The number of ethylene oxide (EO) and/or propylene oxide (PO) units in these non-ionic surfactants usually varies from 2 to 100, depending on the desired HLB (hydrophilic/lipophilic balance). The number of EO and/or PO units is preferably from 2 to 50.

The ethoxylated or ethoxy-propoxylated fatty alcohols generally comprise from 6 to 22 carbon atoms, the EO and PO units being excluded from these numbers, and are preferably ethoxylated.

The ethoxylated or ethoxy-propoxylated triglycerides can be triglycerides of plant or animal origin (such as lard, tallow, groundnut oil, butter oil, cottonseed oil, linseed oil, olive oil, fish oil, palm oil, grapeseed oil, soybean oil, castor oil, rapeseed oil, copra oil or coconut oil) and are preferably ethoxylated.

The ethoxylated or ethoxy-propoxylated fatty acids are esters of fatty acids (such as, for example, oleic acid or stearic acid) and are preferably ethoxylated.

The ethoxylated or ethoxy-propoxylated esters of sorbitan are cyclized esters of sorbitol with $C_{10}$ to $C_{20}$ fatty acids, such as lauric acid, stearic acid or oleic acid, and are preferably ethoxylated.

The term ethoxylated triglyceride is directed, in the present invention, both at the products obtained by ethoxylation of a triglyceride with ethylene oxide and those obtained by transesterification of a triglyceride with a polyethylene glycol.

Likewise, the term ethoxylated fatty acid includes both the products obtained by ethoxylation of a fatty acid with ethylene oxide and those obtained by transesterification of a fatty acid with a polyethylene glycol.

The ethoxylated or ethoxy-propoxylated fatty amines generally have from 10 to 22 carbon atoms, the EO and PO units being excluded from these numbers, and are preferably ethoxylated.

The ethoxylated or ethoxy-propoxylated alkylphenols generally have 1 or 2 linear or branched alkyl groups having 4 to 12 carbon atoms, in particular octyl, nonyl or dodecyl groups.

The compositions according to the invention can additionally contain all the ingredients appropriate to the development of the compositions intended for seed treatment, such as dyes, inorganic or polymeric thickeners, penetrating and retaining agents, antifoaming agents, stabilizers, antifreezes, preservatives, sequestrants and/or buffer solutions.

The compositions according to the invention can be provided in solid or liquid forms.

Mention may be made, as solid composition forms, of dustable powders, wettable powders, dispersible granules or effervescent tablets or lozenges.

Mention may more especially be made, as liquid composition forms, of dilute aqueous suspensions, aqueous suspension concentrates, pastes, gels or aqueous dispersions.

Liquid compositions are preferred and aqueous suspensions are particularly advantageous because of their ease of use during their application to the seeds.

In this case, and according to a very particularly preferred alternative form of the invention, the agrochemical compositions have an active material content of between 4 and 50%, preferably between 5 and 20%, enabling them to be advantageously stored and transported.

In this case again, it is preferable to use, as non-ionic surface-active agent, at least one ethoxylated or ethoxy-propoxylated di(1-phenylethyl)-phenol or alternatively org tri(1-phenylethyl)phenol which is also ethoxylated or ethoxy-propoxylated. The aqueous suspensions then exhibit an advantageously high active material concentration, at the same time as a homogeneity and an ease of flow which further improve the use thereof, including after storage.

The agrochemical compositions according to the invention can be applied to the seeds by any means known per se, such as by steeping, spraying, soaking or mixing, and cover both commercializable compositions suitable for storage and for transportation, which are diluted with water before application, and treatment liquids applied directly to the seeds.

The compositions according to the invention can be prepared according to techniques well known to a person skilled in the art. Thus, the solid compositions in the powder state can be prepared by intimately mixing the ingredients in the finely divided state and then by milling with mills or other appropriate grinders. The water-dispersible granules can be obtained by extrusion, by compacting or by granulation from a powder, or alternatively by spraying or atomizing an aqueous suspension. As regards the liquid compositions, these are also prepared by mixing the ingredients and fine milling, for example by means of a bead mill, so as to obtain a stable and homogeneous fluid product which does not contain solid sediment.

Another subject of the invention is a method for the agrochemical treatment of rice crops by application to seeds, which have optionally been subjected beforehand to a pregermination phase, of one or more agrochemical active materials, characterized in that the agrochemical active material or materials are applied by means of a composition which is the subject of the invention as defined above.

The agrochemical treatment method according to the invention preferably makes use of a phase of pregermination of the seeds, followed by the application to these seeds of one or more agrochemical active materials and by the prolongation of the phase of pregermination of the seeds thus treated before sowing, characterized in that the agrochemical active material or materials are applied by means of one of the compositions which are the subjects of the invention as defined above.

The initial pregermination phase is often carried out by steeping the rice grains or seeds in water for a time generally of between 24 and 48 hours and at a temperature varying between 25° C. and 35° C. The prolongation of the pregermination phase, after application of the agrochemical treatment, is usually accomplished by allowing the pregerminated and treated seeds to stand for 24 to 48 hours before sowing and by regularly sprinkling the seeds with water during this period, for example every 5 to 8 hours.

The precise conditions under which these phases of pregermination and of prolongation of pregermination are carried out can, however, vary depending on the practices and techniques of the rice growers.

The agrochemical active material or materials are generally applied by immersion, soaking, mixing or spraying with one of the compositions according to the invention or by any other means known to a person skilled in the art.

The invention further relates to rice seeds optionally pregerminated and coated and/or impregnated with one of the compositions according to the invention. Such seeds and the seedlings which result therefrom respectively exhibit normal germination and normal growth and are in addition advantageously protected against major diseases and/or pests of rice, including after regular sprinkling with water throughout the pregermination period, before sowing.

The rice seeds which are the subjects of the invention are preferably pregerminated and coated and/or impregnated with one of the compositions according to the invention.

Finally, the invention relates to a mass, or collection, of juxtaposed rice seeds which are optionally pregerminated and which are coated and/or impregnated with one of the compositions according to the invention. Such a mass, in particular placed in a water-permeable bag, such as a bag made of a woven fibre of a polymeric material, can advantageously be subjected to regular sprinkling with water during the pregermination before sowing, with a very limited risk of dispersion of the agrochemical active material into the environment.

The rice seeds forming the mass, or collection, which is the subject of the invention are preferably pregerminated and coated and/or impregnated with one of the compositions according to the invention.

The following examples, given without implied limitation, illustrate the invention and show how it can be implemented.

EXAMPLE 1

Composition comprising 5% of Compound A:

An aqueous suspension is prepared from Compound A in the finely divided state, this suspension comprising the following ingredients (content expressed as % weight/weight):

| Compound A | 5% |
|---|---|
| Polyethyleneimine with a molar mass of 750,000 g | 0.5% |
| Fatty alcohol condensed with 6 E.O. | 0.1% |
| Tristyrylphenol condensed with 16 E.O. | 0.4% |
| Hydroxyethylcellulose | 0.6% |
| 1,2-Benzisothiazolin-3-one | 0.3% |
| Red pigment | 2% |
| Propylene glycol | 5% |
| Antifoaming agent based on silicone oil | 0.2% |
| Water | 85.9% |

The size of the particles of Compound A in this suspension was reduced to approximately 3 $\mu$m by passing through a bead mill.

In respect of the above aqueous suspension, an adhesion after sprinkling over rice seeds is measured, according to the test defined above, which is equal to 80%. This result is particularly advantageous with respect to that which is obtained for a composition which is analogous in every respect but which does not contain polyethyleneimine, namely an adhesion after sprinkling of 35%.

This composition has a homogeneous appearance and flows readily after storage for 15 days at room temperature or at a temperature of 35° C.

EXAMPLE 2

Example 1 is repeated, the polyethyleneimine dose in the final composition being replaced by 0.3% and the amount of water being consequently modified.

The same result with respect to the appearance and the flow of the suspension and an adhesion after sprinkling of 73% are obtained.

EXAMPLE 3

Example 1 is repeated, the polyethyleneimine dose in the final composition being replaced by 0.15% and the amount of water being consequently modified.

The same result with respect to the appearance and the flow of the suspension and an adhesion after sprinkling of 35% are obtained.

EXAMPLE 4

Example 1 is repeated, the polyethyleneimine dose in the final composition being replaced by 0.7% and the amount of water being consequently modified.

The same result with respect to the appearance and the flow of the suspension and an adhesion after sprinkling of 72% are obtained.

EXAMPLE 5

Example 1 is repeated, the polyethyleneimine dose in the final composition being replaced by 1.7% and the amount of water being consequently modified.

The same result with respect to the appearance and the flow of the suspension and an adhesion after sprinkling of 69% are obtained.

EXAMPLE 6

Example 1 is repeated, the dispersing agent being replaced by a copolymer of ethylene oxide and of propylene oxide with a viscosity of 3000 mPa.s.

The same result with respect to the appearance and the flow of the suspension and an adhesion after sprinkling of 55% are obtained.

EXAMPLE 7

Example 1 is repeated, the dispersing agent being replaced by a copolymer of ethylene oxide and of propylene oxide with a viscosity of 1500 mPa.s.

The same result with respect to the appearance and the flow of the suspension and an adhesion after sprinkling of 65% are obtained.

EXAMPLE 8

Example 1 is repeated, the dose of polyethyleneimine with a molar mass of 750,000 in the final composition being replaced by 1.2% of polyethyleneimine with a molar mass of 2,000,000 and the amount of water being consequently modified.

The same result with respect to the appearance and the flow of the suspension and an adhesion after sprinkling of 60% are obtained.

EXAMPLE 9

Composition comprising 1% of Compound A

A Compound A suspension concentrate (Suspension A) is first of all prepared by mixing the ingredients and fine milling, this suspension concentrate comprising:

| Compound A | 50% |
|---|---|
| Ethoxylated alcohol (6 E.O.) | 1% |
| Potassium salt of tristyrylphenol phosphate (16 E.O.) | 5% |
| Propylene glycol | 5% |
| Antifoaming agent based on silicone oil | 0.7% |
| Xanthan gum | 0.2% |
| 1,2-Benzothiazolin-3-one | 0.02% |
| Water | 38.08% |

A dilute suspension comprising 1% of Compound A is then prepared in the following way:

| Suspension A | 2% |
|---|---|
| Red pigment | 0.5% |
| Polyethyleneimine with a molar mass of 800 g | 0.33% |
| Water | 97.17% |

An adhesion after sprinkling (according to the test defined above) of 55% is measured. The adhesion after sprinkling of the dilute suspension obtained without addition of polyethyleneimine is 35%.

EXAMPLE 10

Example 9 is repeated, the dose of polyethyleneimine with a molar mass of 800 g in the dilute suspension being replaced by 0.25% of polyethyleneimine with a molar mass of 2000 g and the amount of water being consequently modified.

An adhesion after sprinkling of 78% is measured.

EXAMPLE 11

Example 9 is repeated, the dose of polyethyleneimine with a molar mass of 800 g in the dilute suspension being replaced by 0.16% of polyethyleneimine with a molar mass of 25,000 g and the amount of water being consequently modified.

An adhesion after sprinkling of 79% is measured.

EXAMPLE 12

Example 9 is repeated, the dose of polyethyleneimine with a molar mass of 800 g in the dilute suspension being replaced by 0.12% of polyethyleneimine with a molar mass of 750,000 g and the amount of water being consequently modified.

An adhesion after sprinkling of 90% is measured.

EXAMPLE 13

Influence of the Agrochemical Compositions of the Invention on the Growth of Rice This test makes it possible to evaluate the influence of the agrochemical compositions of the invention on the growth of rice with respect to seeds treated without these agrochemical compositions.

Equipment and methods:

Rice seeds of the Koshihikari variety are subjected to pregermination for 36 hours in water at laboratory temperature and then half are treated with the composition defined in Example 1 and half are treated with this same composition not containing polyethyleneimine.

Four hours after treatment, in order that they can drain and thus allow easier sowing, these seeds are sown in trays, either in peat-rich compost or in soil from the Camargue. These seeds are either sown at a high density (10 g/tray of 110.5 $cm^2$) or sown 25 per tray. In all cases, each tray is placed in water (simulation of rice-paddy conditions) after emergence of the seedlings.

The growth of the plants is monitored under glass, either in a controlled-environment chamber maintained day and night at 20° C. or in a chamber corresponding to a 12/12 photoperiod at temperatures of 24° C. during the day and of 16° C. during the night. The selectivity is assessed by measurement of the size of the plants 19 days after treatment, which size is estimated overall in the case of the dense sowings, or seedling by seedling in the case of the trays sown with 25 seeds.

In parallel with the sowing, 20 seeds of each batch are placed in petri dishes on moistened filter paper in order to assess the germination energy of these seeds 48 hours after treatment at 23–25° C. The germination energy score is calculated as a function of the number of seeds which have or have not germinated and, for those which have germinated, as a function of the classes of size of the radicle from 5 mm in 5 mm units.

Results:

1) Germination energy
   Each treatment was repeated twice.
   No difference is recorded between the treatment with the composition of example 1 without polyethyleneimine and the composition of example 1 with polyethyleneimine.

2) effect on growth under glass
   No significant difference is recorded between the estimated overall size of the plants from different trays treated with the agrochemical composition of Example 1, whether or rot it contains polyethyleneimine, for tests carried out on compost or on soil from the Camargue and under rice-paddy conditions.

What is claimed is:

1. An agrochemical composition comprising from 0.5 to 50% by weight of at least one agrochemical active material of formula (I):

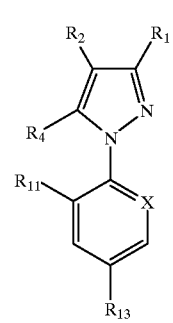

in which:

$R_1$ represents a halogen atom or a CN or methyl group;

$R_2$ represents $S(O)_n R_3$ or 4, 5-dicyanoimidazol-2-yl or haloalkyl;

$R_3$ represents alkyl or haloalkyl;

$R_4$ represents a hydrogen or halogen atom or an $NR_5R_6$, $S(O)_mR_7$, $C(O)R_7$ or $C(O)O-R_7$, alkyl, haloalkyl or $OR_8$ radical or an $-N=C(R_9)(R_{10})$ radical;

$R_5$ and $R_6$ independently represent a hydrogen atom or an alkyl, haloalkyl, $C(O)$ alkyl, $C(O)$ $OR_7$ or $S(O)_rCF_3$ radical or $R_5$ and $R_6$ can together form a divalent alkylene radical which can be interrupted by one or two divalent heteroatoms, such as oxygen, nitrogen or sulphur;

$R_7$ represents an alkyl or haloalkyl radical;

$R_8$ represents an alkyl or haloalkyl radical or a hydrogen atom;

$R_9$ represents an alkyl radical or a hydrogen atom;

$R_{10}$ represents a phenyl or heteroaryl group optionally substituted by one or more halogen atoms or groups such as OH, —O-alkyl, —S-alkyl, cyano or alkyl;

$R_{11}$ and $R_{12}$ represent, independently of one another, a hydrogen or halogen atom or CN or $NO_2$;

$R_{13}$ represents a halogen atom or a haloalkyl, haloalkoxy, $S(O)_qCF_3$ or $SF_5$ group;

m, n, q and r represent, independently of one another, and integer equal to 0, 1 or 2;

X represents a trivalent nitrogen atom or a $C-R_{12}$ radical, the other three valencies of the carbon atom forming part of the aromatic ring;

with the proviso that, when $R_1$ is methyl, then either $R_3$ is haloalkyl, $R_4$ is $NH_2$, $R_{11}$ is Cl, $R_{13}$ is $CF_3$ and X is N or else $R_2$ is 4, 5-dicyanoimidazol-2-yl, $R_4$ is Cl, $R_{11}$ is Cl, $R_{13}$ is $CF_3$ and X is C—Cl, and an effective amount, of a high molar-mass hyperbranched polymer wherein said polymer is selected from the group consisting of polyethyleneamines, polyamidoamides, polyethyleneimines, polyethers, and copolymers thereof.

2. An agrochemical composition according to claim 1, wherein said composition comprises from 1 to 20% by weight of at least one agrochemical material of formula (I).

3. An agrochemical composition according to claim 1, wherein said hyperbranched polymer has a molar mass of from 300 to 3,000,000.

4. An agrochemical composition according to claim 1, wherein said hyperbranched polymer has a molar mass of from 800 to 2,000,000.

5. An agrochemical composition according to claim 1, wherein said hyperbranched polymer is a polyethyleneimine.

6. An agrochemical composition according to claim 1, wherein said effective amount of hyperbranched polymer corresponds to a weight of polymer/weight of agrochemical active material ratio of from 0.01 to 5.

7. An agrochemical composition according to claim 6, wherein said effective amount of hyperbranched polymer corresponds to a weight of polymer/weight of agrochemical active material ratio of from 0.01 to 0.5.

8. An agrochemical composition according to claim 1, wherein said material of formula (I) is such that $R_1$ is CN and/or $R_3$ is haloalkyl and/or $R_4$ is $NH_2$ and/or $R_{11}$ and $R_{12}$ are, independently of one another, a halogen atom and/or $R_{13}$ is haloalkyl.

9. An agrochemical composition according to claim 1, wherein said material of formula (I) is 1-[2,6-$Cl_2$-4-$CF_3$phenyl]-3-CN-4-[SO—$CF_3$]-5-$NH_2$pyrazole.

10. An agrochemical composition according to claim 1, further comprising one or more other agrochemical active materials other than said material of formula (I) used in rice cultivation.

11. An agrochemical composition according to claim 10, wherein said other agrochemical active material is an agent for the protection of plants, an agent for the nutrition of plants, a herbicide, fungicide, insecticide, or growth regulator.

12. An agrochemical composition according to claim 1, further comprising one or more agriculturally acceptable solid or liquid vehicles and/or one or more agriculturally acceptable surface-active agents.

13. An agrochemical composition according to claim 1, wherein said composition is in liquid form.

14. A method for the agrochemical treatment of rice crops comprising the application of at least one agrochemical active material to rice seeds, wherein said agrochemical active material comprises said material of claim 1.

15. An agrochemical treatment method according to claim 14, wherein said seeds have been subjected, before said agrochemical treatment, to a pregermination phase.

16. A method for the agrochemical treatment of rice crops comprising the steps of pregermination of rice seeds, application to said seeds of at least one agrochemical active material, additional pregermination of said seeds before sowing, wherein said agrochemical active material is a composition comprising the composition of claim 1.

17. A treatment method according to claim 14, wherein said application is by immersion, soaking, mixing or spraying.

18. Rice seed coated and/or impregnated with a composition comprising the composition of claim 1.

19. Rice seed according to claim 18, wherein said rice seed has been subjected to a pregermination phase before said coating and/or impregnation.

20. Mass, or collection, of juxtaposed rice seeds which are coated and/or impregnated with composition comprising the composition according to claim 1.

21. Mass, or collection, of rice seeds according to claim 20, wherein said seeds have been subjected to a pregermination phase before said coating and/or impregnation.

22. An agrochemical composition according to claim 13, wherein said liquid form is an aqueous suspension.

* * * * *